(12) United States Patent
Kirkland et al.

(10) Patent No.: US 10,590,162 B2
(45) Date of Patent: Mar. 17, 2020

(54) REVERSIBLE METAL ION CHELATORS

(71) Applicant: PROMEGA CORPORATION, Madison, WI (US)

(72) Inventors: Thomas Kirkland, Atascadero, CA (US); Mark McDougall, Arroyo Grande, CA (US); Poncho Meisenheimer, San Luis Obispo, CA (US); Min Zhou, San Luis Obispo, CA (US)

(73) Assignee: PROMEGA CORPORATION, Madison, WI (US)

( * ) Notice: Subject to any disclaimer, the term of this patent is extended or adjusted under 35 U.S.C. 154(b) by 262 days.

(21) Appl. No.: 15/322,519

(22) PCT Filed: Jul. 2, 2015

(86) PCT No.: PCT/US2015/039036
§ 371 (c)(1),
(2) Date: Apr. 7, 2017

(87) PCT Pub. No.: WO2016/004333
PCT Pub. Date: Jan. 7, 2016

(65) Prior Publication Data
US 2017/0137456 A1    May 18, 2017

Related U.S. Application Data

(60) Provisional application No. 62/020,227, filed on Jul. 2, 2014.

(51) Int. Cl.
*C07H 21/04* (2006.01)
*C12Q 1/6816* (2018.01)
(Continued)

(52) U.S. Cl.
CPC .............. *C07H 21/04* (2013.01); *C07H 21/00* (2013.01); *C12N 9/1252* (2013.01); *C12Q 1/686* (2013.01);
(Continued)

(58) Field of Classification Search
CPC ...... C07H 21/00; C07H 21/04; C12Q 1/6848; C12Q 1/6816
(Continued)

(56) References Cited

U.S. PATENT DOCUMENTS

| 8,026,058 B2 | 9/2011 | Ankenbauer et al. |
| 2002/0182227 A1 | 12/2002 | Halstead |
| 2008/0269065 A1 | 10/2008 | Lyon et al. |

FOREIGN PATENT DOCUMENTS

| WO | WO 2007/065007 | 6/2007 |
| WO | WO 2013/080154 | 6/2013 |

(Continued)

OTHER PUBLICATIONS

Carter et al., Fluorescent sensors for measuring metal ions in living systems. Chem Rev. Apr. 23, 2014;114(8):4564-601.
(Continued)

*Primary Examiner* — Jezia Riley
(74) *Attorney, Agent, or Firm* — Casimir Jones SC; David W. Staple

(57) ABSTRACT

Provided herein are chelator constructs (e.g., nucleic acid, peptide, peptide nucleic acid, etc.) that sequester metal ions (e.g., $Mg^{2+}$) under a first set of conditions and fail to sequester or release sequestered metal ions under a second set of conditions. In particular, nucleic acid constructs are provided that sequester metal ions (e.g., $Mg^{2+}$) under conditions that favor secondary and tertiary structure formation
(Continued)

and release or fail to sequester metal ions under conditions that disfavor the formation of such structures.

13 Claims, 8 Drawing Sheets

Specification includes a Sequence Listing.

(51) Int. Cl.
  *C07H 21/00* (2006.01)
  *C12N 9/12* (2006.01)
  *C12Q 1/6848* (2018.01)
  *C12Q 1/686* (2018.01)
(52) U.S. Cl.
  CPC ......... *C12Q 1/6816* (2013.01); *C12Q 1/6848* (2013.01); *C12Y 207/07007* (2013.01)
(58) Field of Classification Search
  USPC ....................................................... 435/6.12
  See application file for complete search history.

(56) References Cited

FOREIGN PATENT DOCUMENTS

| WO | WO 2013/185081 | 12/2013 |
| WO | WO 2016/004333 | 1/2016 |

OTHER PUBLICATIONS

Ceska et al., Structure-specific DNA cleavage by 5' nucleases. Trends Biochem Sci. Sep. 1998;23(9):331-6.
Chase et al., Exonuclease VII of *Escherichia coli*. Purification and properties. J Biol Chem. Jul. 25, 1974;249(14):4545-52.
Hyman et al., Probing oxidative stress: Small molecule fluorescent sensors of metal ions, reactive oxygen species, and thiols. Coord Chem Rev. Oct. 1, 2012;256(19-20):2333-2356.
Lyamichev et al., Comparison of the 5' nuclease activities of taq DNA polymerase and its isolated nuclease domain. Proc Natl Acad Sci U S A. May 25, 1999;96(11):6143-8.
Lyamichev et al., Structure-specific endonucleolytic cleavage of nucleic acids by eubacterial DNA polymerases. Science. May 7, 1993;260(5109):778-83.
Maguire et al., Magnesium chemistry and biochemistry. BioMetals. 2002;15:203-10.
Montgomery et al., Influence of PCR reagents on DNA polymerase extension rates measured on real-time PCR instruments. Clin Chem. Feb. 2014;60(2):334-40.
Morgan et al., Reversible metal-dependent destabilization and stabilization of a stem-chelate-loop probe binding to an unmodified DNA target. Bioconjug Chem. Oct. 17, 2012;23(10):2020-4.
Patton, Development and Applications of Click Chemistry, seminar abstract, Nov. 8, 2004, 8 pages.
Que et al., Metals in Neurobiology: Probing Their Chemistry and Biology with Molecular Imaging. Chem Rev. May 2008;108(5):1517-49.
Sambrook et al. (1989) Molecular Cloning: A Laboratory Manual (2nd Edition). pp. 10.51-10.52.
Trapani et al., Intracellular magnesium detection: imaging a brighter future. Analyst. Aug. 2010;135(8):1855-66.
International Search Report and Written Opinion for PCT/US2015/039036, dated Jan. 12, 2016, 14 pages.

Molecule 1: 5'-C-C-C-T-T-C-T(di-acid)-3' (SEQ ID NO: 1)
Molecule 2: 5'-(di-acid)T-C-C-T-T-C-T-T-3' (SEQ ID NO: 2)
Molecule 3: 5'-A-A-G-A-A-G-G-A-A-G-A-A-G-G-G-3' (SEQ ID NO: 3)

Molecule 1

Molecule 2

Molecule 3

Molecule 1: 5'-C-C-C-T-T-C-T-T-C-C-T-T-C-T-T-T(di-acid)-3' (SEQ ID NO: 4)
Molecule 2:: 5'-(di-acid)A-A-A-G-A-A-G-A-A-G-A-A-G-A-A-G-G-3' (SEQ ID NO: 5)

Molecule 1

Molecule 2

REVERSIBLE METAL ION CHELATORS

CROSS-REFERENCE TO RELATED APPLICATIONS

The present invention claims priority to U.S. Provisional Patent Application Ser. No. 62/020,227, filed Jul. 2, 2014, which is incorporated by reference in its entirety.

FIELD

Provided herein are chelator constructs that sequester metal ions under a first set of conditions and fail to sequester or release sequestered metal ions under a second set of conditions.

BACKGROUND

Chelation involves the formation or presence of two or more separate coordinate bonds between a polydentate ligand and a single central metal ion. Chelators are used in a variety of applications to remove metal ions from solution.

SUMMARY

Provided herein are chelator constructs (e.g., comprising nucleic acid, peptide, peptide nucleic acid, etc.) that sequester metal ions (e.g., $Mg^{2+}$, $Zn^{2+}$, $Ca^{2+}$, $Mn^{2+}$, etc.) under a first set of conditions (e.g., low temperature, high salt, high pH, etc.) and fail to sequester or release sequestered metal ions under a second set of conditions (e.g., high temperature, low salt, neutral pH, etc.). In particular, biopolymers (e.g., nucleic acid constructs, peptide constructs, etc.) are provided that sequester metal ions (e.g., $Mg^{2+}$, $Zn^{2+}$, $Ca^{2+}$, $Mn^{2+}$, etc.) under conditions that favor secondary and tertiary structure formation and release or fail to sequester metal ions under conditions that disfavor the formation of such structures.

In some embodiments, provided herein are reversible chelator constructs comprising one or more structural moieties attached to two or more chelation components (e.g., 2, 3, 4, 5, 6, 7, 8, etc.), wherein under a first set of conditions (e.g., high temperature conditions) said one or more structural moieties adopt a first conformation that positions and/or orients said two or more chelation components such that said two or more chelation components are unable to efficiently chelate metal ions (e.g., chelate less efficiently), and wherein under a second set of conditions (e.g., low temperature conditions) said one or more structural moieties adopt a second conformation that positions and/or orients said two or more chelation components such that said two or more chelation components efficiently chelate metal ions (e.g., more efficiently chelate metal ions). In some embodiments, the one or more structural moieties are selected from peptides, nucleic acids, and peptide-nucleic acids. In some embodiments, the one or more structural moieties are nucleic acids.

In some embodiments, the reversible chelator construct comprises a single structure-forming nucleic acid strand and two chelation components, wherein formation of the structure brings the chelation components into appropriate proximity and orientation to efficiently chelate metal ions and wherein melting of the structure separates the chelation components such that said chelation components are unable to efficiently chelate metal ions. In some embodiments, the chelation components are attached to 5' and 3' termini of the nucleic acid strand. In some embodiments, the chelation components are attached to the nucleic acid strand internally. In some embodiments, chelation components are attached to the nucleic acid strand by a linker. In some embodiments, the structure is selected from a stem-loop, hairpin, cruciform, triple helix, pseudoknot, two-stem junctions, etc.

In some embodiments, the reversible chelator construct comprises a first biopolymer (e.g., first nucleic acid strand) attached to a first chelation component and a second biopolymer (e.g., second nucleic acid strand attached to a second chelation component), wherein the first and second nucleic acid strands are complementary, wherein hybridization of the nucleic acid strands brings the chelation components into appropriate proximity and orientation to efficiently chelate metal ions, and wherein melting of the nucleic acid strands separates the chelation components such that said chelation components are unable to efficiently chelate metal ions. In some embodiments, the first chelation component is attached to the 5' end of the first nucleic acid strand and the second chelation component is attached to the 3' end of the second nucleic acid strand. In some embodiments, the chelation components are attached to the nucleic acid strands internally. In some embodiments, chelation components are attached to the nucleic acid strands by linkers.

In some embodiments, the reversible chelator construct comprises a nucleic acid strand that is not attached to a chelation component and one or more nucleic acid strands attached chelation components, wherein hybridization of the one or more nucleic acid strands to chelation components to the nucleic acid strand not attached to a chelation component brings the chelation components into appropriate proximity and orientation to efficiently chelate metal ions, wherein melting of the nucleic acid strands separates the chelation components such that said chelation components are unable to efficiently chelate metal ions.

In some embodiments, the two or more chelation components are iminodiacetic acid moieties, A23187 moieties, phosphate (e.g., a phosphate moiety added to a structural moiety, a 5' phosphate of a nucleic acid strand, etc.), acetic acid, polyether (PEG), thioether, thiol, amine, heterocyclic amine such as pyridine, bipyridine, terpyridine, phenanthroline, etc. In some embodiments, a chelation moiety comprises any compound, functional group, molecule, macromolecule, ionophore, etc. that is (1) capable of efficiently chelating one or more types of metal ions, and (2) divisible into two or more chelation components that are separately incapable of efficient metal-ion chelation, but are capable of efficient metal-ion chelation when properly positioned (e.g., within a particular distance) and oriented.

In some embodiments, high temperature is a temperature above a transition temperature between the first and second conformations. In some embodiments, low temperature is a temperature below a transition temperature between the first and second conformations.

In some embodiments, less efficient chelation is a $K_d$ of 10 µM or more, 50 µM or more, 100 µM or more, 200 µM or more, 500 µM or more, or 1 mM or more. In some embodiments, more efficient chelation is a $K_d$ of 1 µM or less, 500 nM or less, 200 nM or less, 100 nM or less, 50 nM or less, 10 nM or less, or 1 nm or less.

In some embodiments, less efficient chelation refers to an affinity for metal ions that is less (e.g., 2-fold less, 3-fold less, 4-fold less, 5-fold less, 10-fold less, 20-fold less, 50-fold less, 100-fold less, 1000-fold less, etc.) than the affinity of the other components of the system or reaction (e.g., DNA polymerase, DNA, nucleotides, etc.) for the sample metal ions. In some embodiments, more efficient chelation refers to an affinity for metal ions that is greater (e.g., 2-fold more, 3-fold more, 4-fold more, 5-fold more, 10-fold more, 20-fold more, 50-fold more, 100-fold more, 1000-fold more, etc.) than the affinity of the other components of the system or reaction (e.g., DNA polymerase, DNA, nucleotides, etc.) for the sample metal ions.

In some embodiments, the affinity of a chelator construct for a metal ion (e.g., $Mg^{2+}$, $Zn^{2+}$, $Ca^{2+}$, $Mn^{2+}$, etc.) in the chelation conformation (e.g., more efficient chelation conformation) is at least one log higher affinity (e.g., >2 logs higher affinity, >3 logs higher affinity, >4 logs higher affinity, >5 logs higher affinity, >6 logs higher affinity, >7 logs higher affinity, >8 logs higher affinity, or more) than in the release or non-chelation conformation (e.g., more efficient chelation conformation). In some embodiments, the affinity of a chelator construct for a metal ion (e.g., $Mg^{2+}$, $Zn^{2+}$, $Ca^{2+}$, $Mn^{2+}$, etc.) in the chelation conformation (e.g., more efficient chelation conformation) is between two and six logs higher than in the release or non-chelation conformation (e.g., more efficient chelation conformation).

In some embodiments, the provided herein are methods of regulating an enzymatic reaction comprising: (a) providing in a reaction mix: (i) an enzyme that catalyzes said enzymatic reaction, wherein said enzyme employs a metal ion cofactor for catalysis; (ii) a substrate for said enzyme; (iii) optionally any other reactants for said enzymatic reaction; (iv) the metal ion cofactor for said enzyme; and (v) a reversible chelator construct that is incapable of efficiently chelating said metal ion cofactor under a first set of conditions and more efficiently chelates said metal ion cofactor under a second set of conditions; (b) exposing said reaction mix to said first set of conditions, wherein said enzyme less efficiently catalyzes said enzymatic reaction (e.g., reaction rate is $<\frac{1}{2}V_{max}$, $<\frac{1}{4}V_{max}$, $<\frac{1}{8}V_{max}$, $<\frac{1}{16}V_{max}$, $<\frac{1}{32}V_{max}$, $<\frac{1}{64}V_{max}$, $<\frac{1}{100}V_{max}$, $<\frac{1}{1000}V_{max}$, or less) under said first set of conditions because said metal ion cofactor is chelated by the reversible chelator construct; and (c) exposing said reaction mix to said second set of conditions, wherein said enzyme catalyzes said enzymatic reaction under said second set of conditions because said metal ion cofactor is available in solution.

In some embodiments, step (b) is performed before step (c). In some embodiments, the method further comprises: (d) repeating step (b).

In some embodiments, step (c) is performed before step (b). In some embodiments, the method further comprises: (d) repeating step (c).

In some embodiments, the enzyme is DNA polymerase said metal ion cofactor is magnesium. In some embodiments, the enzymatic reaction is polymerase chain reaction. In some embodiments, the enzymatic reaction is cleavage of nucleic acids (e.g., 3' to 5').

In some embodiments, inefficient catalysis (or less efficient catalysis) is less than 50% enzyme activity (e.g., of maximum enzyme activity), less than 40% enzyme activity, less than 30% enzyme activity, less than 20% enzyme activity, less than 10% enzyme activity, less than 50% enzyme activity, or less than 1% enzyme activity. In some embodiments, efficient catalysis (or more efficient catalysis) is greater than 50% enzyme activity (e.g., of maximum enzyme activity), greater than 60% enzyme activity, greater than 70% enzyme activity, greater than 80% enzyme activity, greater than 90% enzyme activity, greater than 95% enzyme activity, greater than 99% enzyme activity.

In some embodiments, inefficient catalysis is defined as the absence of detectable reaction products (e.g., PCR products, secondary PCR products, 5' to 3' nuclease product, 3' to 5' nuclease product, restriction digest product, etc.). In some embodiments, inefficient catalysis is defined as reduction of detectable reaction products (e.g., PCR products, secondary PCR products, 5' to 3' nuclease product, 3' to 5' nuclease product, restriction digest product, etc.) compared to the reaction performed in the absence of a chelator construct (e.g., <50% of product, <10% of product, <1% of product, <0.5% of product, <0.1 product, etc.). In some embodiments, the amount of detectable reaction products is determined by standard detection methods for the particular reaction. In some embodiments, efficient catalysis is defined as a comparable amount of detectable reaction products (e.g., PCR products, secondary PCR products, 5' to 3' nuclease product, 3' to 5' nuclease product, restriction digest product, etc.) compared to the reaction performed in the absence of a chelator construct (e.g., >50%, >75%, >90%, >95%, >99%, >100%, or more). In some embodiments, the amount of detectable reaction products is determined by standard detection methods for the particular reaction (e.g., gel electrophoresis).

In some embodiments, provided herein are compositions comprising one or more biopolymers and two or more iminodiacetic acid moieties, wherein upon folding and/or hybridization of said one or more biopolymers said two or more iminodiacetic acid moieties are positioned adjacent to one another. In some embodiments, the one or more biopolymers are selected from nucleic acids, peptides, and peptide nucleic acids. In some embodiments, the two or more iminodiacetic acid moieties are attached to the same biopolymer of said one or more biopolymers. In some embodiments, the two or more iminodiacetic acid moieties are attached to the separate biopolymers of said one or more biopolymers.

BRIEF DESCRIPTION OF THE DRAWINGS

FIGS. 2A-I show illustrations of exemplary chelators comprising nucleic acid structural moieties. For each construct (A-I), the conditions on the left favor secondary structure formation and the conditions on the right disfavor secondary structure. (A) Two complementary nucleic acid strands, one with a 5' chelation component and the other with a 3' chelation component that form a chelation moiety when the stands are hybridized. (B) Two complementary nucleic acid strands, each with 5' and 3' chelation components that form two chelation moieties when the stands are hybridized. (C) Two complementary nucleic acid strands, both with internal chelation components that form a chelation moiety when the stands are hybridized. (D) One hairpin forming nucleic acid strand, with 5' and 3' chelation components that form a chelation moiety when the hairpin is formed. (E) One hairpin-forming nucleic acid strand, with two internal chelation components that form a chelation moiety within the stem when the hairpin is formed. (F) One hairpin-forming nucleic acid strand, with internal chelation components that form a chelation moiety within the loop when the hairpin is formed. (G) One pseudoknot-forming nucleic acid strand, with internal chelation components that form a chelation moiety when the pseudoknot is formed. (H) One double-hairpin-forming nucleic acid strand, with 5' and 3' chelation components that form a chelation moiety at a two-stem junction under folding conditions. (I) A first nucleic acid strand with a 5' chelation component, a second nucleic acid strand with a 3' chelation component, and third nucleic acid strand without chelation components; the first and second nucleic acid strands hybridize to the third, forming a chelation moiety when the stands are hybridized.

FIGS. 7A-D show the application of the reversible metal ion chelators to polymerase and 3' to 5' nuclease degradation in PCR. A) With reversible metal ion chelators and at low temperature, the chelators sequesters magnesium rendering the DNA polymerase inactive. B) With reversible metal ion chelators and at high temperature, the magnesium is released and able to activate the DNA polymerase and PCR proceeds. C) Without the reversible metal ion chelators and at low temperature, the magnesium is able to activate the DNA polymerase. At this temperature the polymerase domain of the DNA polymerase can start polymerization of secondary products and primer dimers and the 3' to 5' nuclease domain can degrade primers and template DNA. D) Without the reversible metal ion chelators and at high temperature, the amplification quality is affected by accumulation of secondary products, primer dimers and decreased yield.

DEFINITIONS

Figure 1:
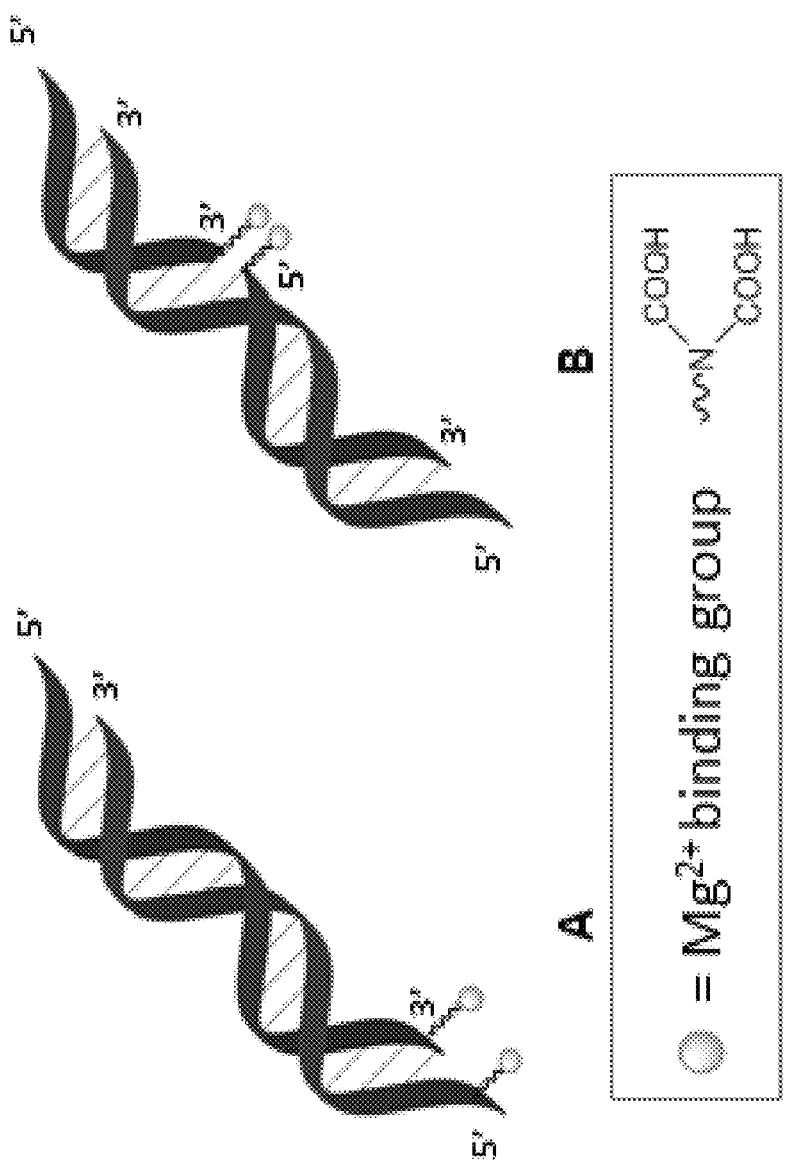
FIG. 1 shows illustrations of exemplary nucleic acid chelator constructs under hybridization/folding conditions, in which chelation components are brought together to form chelator moieties: (A) two nucleic acid structural moieties, both end-labeled with chelator components; (B) three nucleic acid structural moieties, two of which end-modified with chelator components; (C) two nucleic acid structural moieties, both internally-modified with chelator components; and (D) a single nucleic acid structural moiety, internally-modified at two positions with chelator components. In each case, when these exemplary constructs are placed in conditions that disfavor hybridization/folding, the chelation components cease to be in close proximity. (E) shows an illustration of base pairing in a double stranded DNA and the dimensions thereof.
Figure 1:
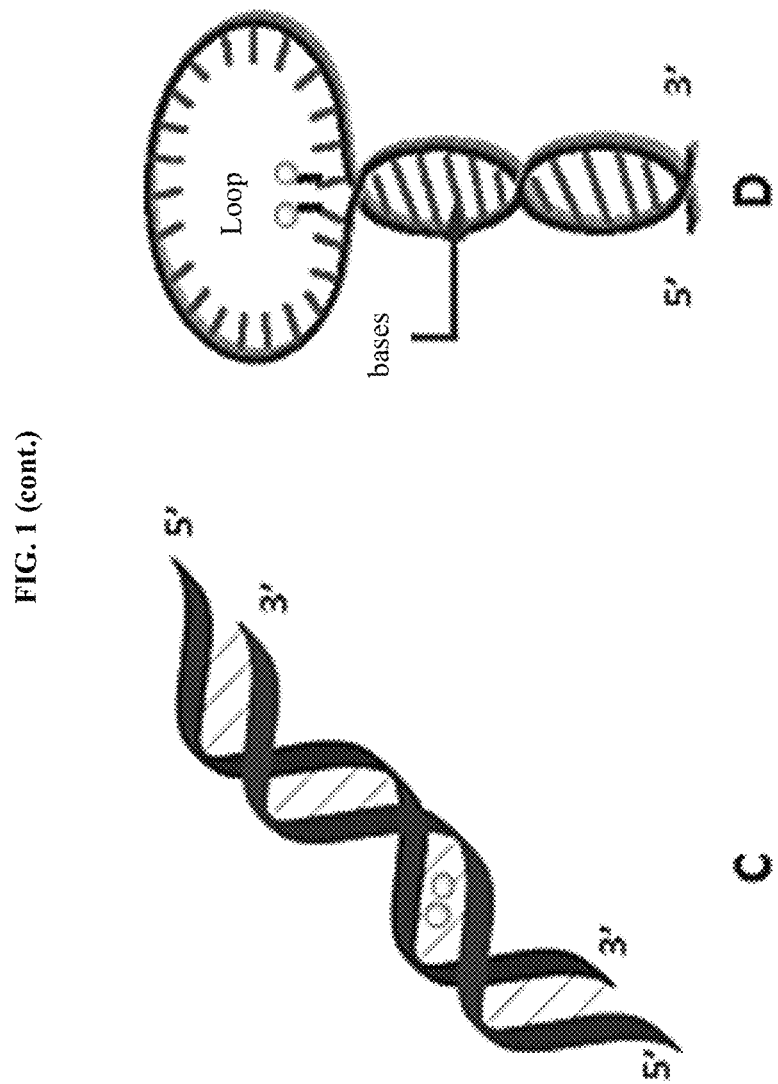
Figure 1:
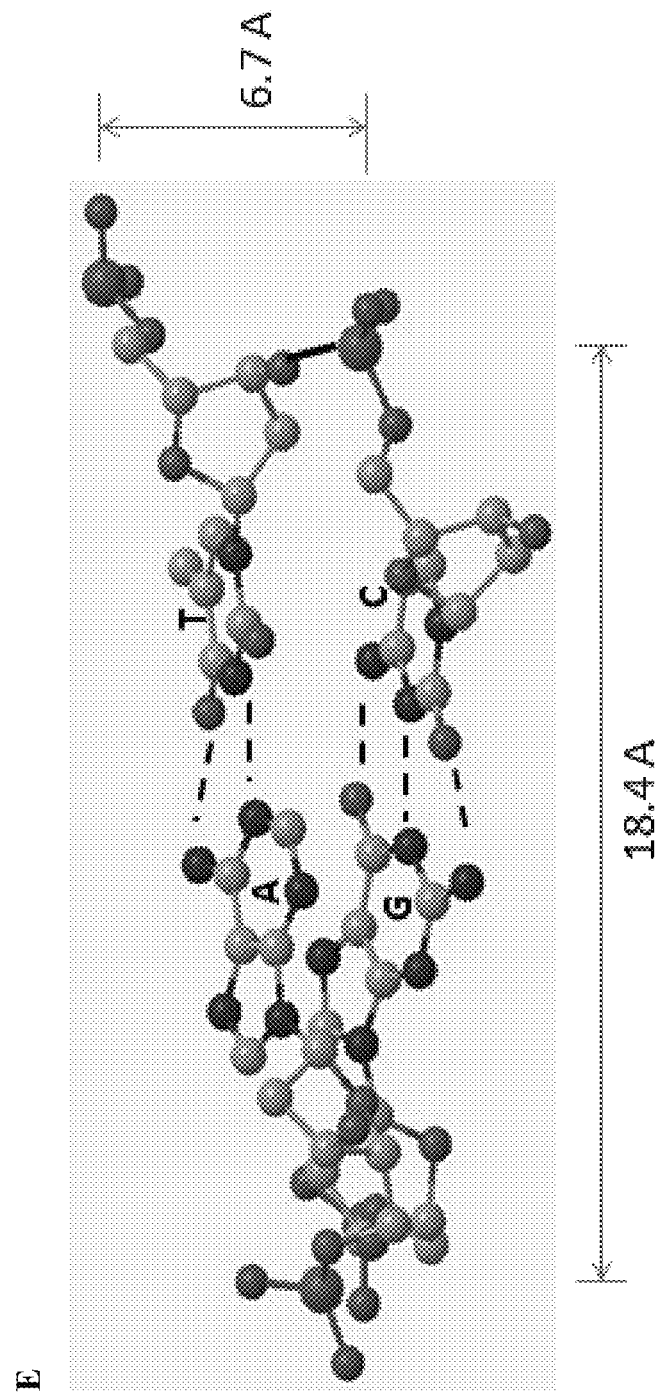

As used herein, the term "chelation moiety" refers to a compound or functional group containing electron-donating groups that can combine by coordinative bonding with a metal ion to form a stable structure. Typically, a chelation moiety is part of a larger molecule or macromolecule. In some embodiments, a chelation moiety comprises two separate compounds or functional groups (e.g., chelation components).

As used herein, the term "chelation component" refers to a compound or functional group, that when brought in close proximity to and/or proper orientation with one or more other chelation components, forms a chelation moiety. A single chelation component is not capable of efficient or stable chelation, as it has insufficient affinity for the metal ion to sequester it (e.g., from participating in a chemical or enzymatic reaction), whereas the full chelation moiety has sufficient affinity. In some embodiments, a chelation moiety is part of a larger molecule or macromolecule.

As used herein, the term "chelator" or "chelator construct" refers to a compound, polymer, complex, or other molecular or macromolecular entity containing electron-donating groups that can combine by coordinative bonding with a metal ion to form a stable structure. A chelator may consist solely of a moiety capable of chelation (e.g., chelation moiety) or may further comprise other molecular or macromolecular portions (e.g., "structural moieties"). In some embodiments, a chelator comprises two or more compounds, polymers, complexes, or other molecular or macromolecular entities that when combined create a structure capable of chelating a metal ion.

As used herein, the term "structural moiety" refers to a compound, polymer, or other molecular or macromolecular entity that adopts secondary, tertiary, and/or quaternary structure under appropriate conditions.

The term "nucleic acid", as used herein, refers to an oligonucleotide, nucleotide or polynucleotide, and fragments or portions thereof, and to DNA or RNA of genomic or synthetic origin which may be single or double stranded, and represent the sense or antisense strand.

The term "nucleic acid strand" refers to a single continuous polymer of nucleotides. A single-stranded nucleic acid is one nucleic acid stand. A double stranded nucleic acid is two complementary nucleic acid stands.

The term "stem loop", also called "hairpin loop", refers to a structure that comprises a double-stranded portion (stem), formed by hydrogen bonding between inverted repeat sequences in a single-stranded nucleic acid molecule, and a loop portion sandwiched in between. A stem may be formed of 2 to 100 base pairs, and a loop may be formed of 3 to 20 nucleotides.

The terms "peptide" and "polypeptide" as used herein refer to polymers of amino acids, of any length and of natural or synthetic origin.

The term "amino acid" refers to naturally occurring and non-naturally occurring amino acids, as well as imino acids such as proline, amino acid analogs and amino acid mimetics that function in a manner similar to the naturally occurring amino acids. Amino acids comprise a central carbon, connected to H, amine, carboxylic acid, and R groups. Typical amino acids differ only at the R position, and the identity of the amino acid (e.g., glycine, alanine, tyrosine, etc.) is defined by the R position. Other modifications of amino acids are within the scope of the invention.

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids. The term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

"Solid support" refers herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly) vinylidenefluoride, polycarbonate, and polymethylpentene.

DETAILED DESCRIPTION

Provided herein are chelator constructs (e.g., comprising nucleic acid, peptide, peptide nucleic acid, etc.) that sequester metal ions (e.g., $Mg^{2+}$, $Zn^{2+}$, $Ca^{2+}$, etc.) under a first set of conditions (e.g., low temperature, high salt, high pH, etc.) and fail to sequester or release sequestered metal ions under a second set of conditions (e.g., high temperature, low salt, neutral pH, etc.).

In certain embodiments, provided herein are constructs (e.g., single polymer, duplex, complex, etc.) that form a metal-ion-chelating structure (e.g., low $K_d$ (e.g. nanomolar, micormolar, etc.)) under a first set of conditions (e.g., structure forming conditions (e.g., low temperature, high salt, neutral pH)) and denature or form a structure that does not chelate metal ions (e.g., high $K_d$ (e.g., micromolar, millimolar, etc.)) under a second set of conditions (e.g., conditions that do not favor the formation of secondary and/or tertiary structures (e.g., high temperature, low salt, high pH)).

Under a first set of conditions (e.g., one or more of high temperature, low salt, and/or high pH, etc.) the chelator construct is unfolded and the chelation components dissociate. For example, under the first set of conditions, a structural moiety or moieties of a chelator construct are denatured and unable to form a tertiary structure necessary/sufficient to properly align/orient the chelation components for efficient chelation. Likewise, under the first set of conditions, a structural moiety or moieties (e.g., nucleic acid strand or strands) of a chelator construct are unhybrized and unable to form a secondary structure necessary/sufficient to properly align/orient the chelation components for efficient chelation. In some embodiments, the first set of conditions includes a temperature above the melting temperature ($T_m$) of the secondary, tertiary, or quaternary structure of the structural moiety or moieties (e.g., $>T_m+1°$ C., $>T_m+2°$ C., $>T_m+3°$ C., $>T_m+4°$ C., $>T_m+5°$ C., $>T_m+6°$ C., $>T_m+7°$ C., $>T_m+8°$ C., $>T_m+9°$ C., $>T_m+10°$ C., $>T_m+15°$ C., $>T_m+20°$ C., or more).

Under a second set of conditions (e.g., one or more of low temperature, high salt, and/or neutral pH, etc.), the chelator construct is folded and the chelation moiety is formed. For example, under the second set of conditions, a structural moiety or moieties of a chelator construct form a tertiary structure necessary/sufficient to properly align/orient the chelation components for efficient chelation. Likewise, under the second set of conditions, a structural moiety or moieties (e.g., nucleic acid strand or strands) of a chelator construct are hybrized and able to form a secondary structure necessary/sufficient to properly align/orient the chelation components for efficient chelation. In some embodiments, the second set of conditions include a temperature below the melting temperature ($T_m$) of the secondary, tertiary, or quaternary structure of the structural moiety or moieties (e.g., $<T_m-1°$ C., $<T_m-2°$ C., $<T_m-3°$ C., $<T_m-4°$ C., $<T_m-5°$ C., $<T_m-6°$ C., $<T_m-7°$ C., $<T_m-8°$ C., $<T_m-9°$ C., $<T_m-10°$ C., $<T_m-15°$ C., $<T_m-20°$ C., or less).

In some embodiments, a chelator construct comprises one or more structural moieties and one or more chelation moieties. Any combination of structural and chelation moieties (e.g., 1:2, 2:1, 2:2, 2:4, 3:2, etc.) are within the scope of the invention.

In some embodiments, a chelator construct comprises two structural moieties, each connected to a chelation component (e.g., a functional group that does not efficiently chelate metal ions alone, but does efficiently chelate metal ions when combined with a second chelation component to form a chelation moiety). When the chelator construct is exposed to conditions that promote folding and/or hybridization, the chelation components are brought together allowing the chelation of metal ions (e.g., allowing efficient chelation of metal ions, low $K_d$). When the chelator construct is exposed to conditions that disfavor folding and/or hybridization, the chelation components are pulled apart (on their respective structural moieties) or reoriented, preventing the chelation components from chelating metal ions (e.g., preventing efficient chelation of metal ions, high $K_d$).

In some embodiments, a chelator construct comprises two chelation components connected to different portions of a single structural moiety (e.g., opposite ends of the structural moiety). When the chelator construct is exposed to conditions that promote folding and/or hybridization, the chelation components are brought together by the folding of the structural moiety, thereby forming a chelation moiety and allowing the chelation of metal ions (e.g., allowing efficient chelation of metal ions, low $K_d$). When the chelator construct is exposed to conditions that disfavor folding and/or hybridization, the chelation moiety is pulled apart into the individual chelation components (on their respective portions of the structural moiety), preventing the chelation of metal ions (e.g., preventing efficient chelation of metal ions, high $K_d$).

In some embodiments, a chelation moiety forms (e.g., from two or more chelation components)), to provide a single site for chelation of metal ions on a chelator construct. In other embodiments, a single chelator construct (comprising one or more structural moieties) comprises multiple sites for metal ion chelation (e.g., multiple chelator moieties or pairs of chelation components).

B. Chelation Moieties

In certain embodiments, a chelation moiety comprises two or more separate chelation components (e.g., iminodiacetic acid moieties) that form a chelation moiety under a first set of conditions, but do not form a chelation moiety under a second set of conditions. In some embodiments, the chelation components are separated in physical space or by orientation under non-chelation conditions but are brought together or re-oriented under chelation conditions to form a chelation moiety. In such embodiments, the ability of the chelation moiety to chelate metal ions is modulated by forming and/or denaturing the chelation moiety. Suitable chelation moieties that find use in such embodiments are compounds, functional groups, moieties, etc. that chelate magnesium ions, including, but not limited to: iminodiacetic acid groups (See, e.g., Trapani et al. *Analyst,* 2010, 135, 1855-1866; herein incorporated by reference in its entirety). Other chelation moieties comprise A23187 moieties, phosphate (e.g., a phosphate moiety added to a structural moiety, a 5' phosphate of a nucleic acid strand, etc.), acetic acid, polyether (PEG), thioether, thiol, amine, heterocyclic amine such as pyridine, bipyridine, terpyridine, phenanthroline, etc.

In some embodiments, two or more chelation components are oriented under chelation conditions to form or approximate a known metal-ion chelator. Suitable chelation moieties that are formed or approximated in such embodiments include, but are not limited to: diethylenetriaminepentaacetic acid (DTPA), dimercaprol, ethylenediaminetetraacetic acid (EDTA), EDTA analogs (US 2002/0182227; herein incorporated by reference in its entirety), tetraazacyclododecanetetraacetic acid (DOTA), 2,3-Dimercapto-1-propanesulfonic acid (DMPS), dimercaptosuccinic acid (DMSA), α-Hydroxytropolones (WO 2007065007; herein incorporated by reference in its entirety), penicillamine, deferoxamine, deferasirox, and other chelator moieties that incorporate electron donating atoms such as O, S, P or N as Lewis bases to bind the metal (Engelstad and Wolf, "Contrast Agents", in Magnetic Resonance Imaging, Stark and Bradley, Mosby, St. Louis, 1988, pp. 161-181; herein incorporated by reference in its entirety). In some embodiments, chelation moieties are obtained from other metal binding constructs (See, e.g., Carter et al. Chem. Rev. 2014, 114, 4564-4601; Que et al. Chem Rev. 2008 May; 108(5):1517-49; Hyman and Franz. Coordination Chemistry Reviews 256 (2012) 2333-2356; herein incorporated by reference in their entireties).

In some embodiments, a chelation moiety comprises multiple (e.g., two) iminodiacetic acid components which are brought together (e.g., through folding of a structural moiety and/or hybridization of structural moieties) to form an efficient cation sequesterer (e.g., simulating the structure of EDTA), but do not chelate cations (e.g., efficiently) when apart. In some embodiments, the folding of a structural moiety and/or hybridization of structural moieties brings the iminodiacetic acid components into close enough proximity and/or into the appropriate orientation to efficiently chelate a metal ion (e.g., $Mg^{2+}$).

In some embodiments, a chelation moiety or chelation components for a construct are selected to chelate specific metal ions. For example, two iminodiacetic acid components brought together sequester $Ca^{2+}$, $Fe^{3+}$, and/or $Mg^{2+}$; chelator components brought together to form a DOTA-like structure sequester $Gd^{3+}$; chelator components brought together to form a dimercaprol-like structure sequester arsenic, gold, lead, and/or copper; etc. Depending upon the intended application of the chelator construct, different chelation moieties and/or chelation components are selected.

In some embodiments, a chelator moiety chelates many types of metal ion. In other embodiments, more specific chelator moieties are used. In some embodiments, chelator moieties are used that chelate one or more of: lithium, sodium, potassium, rubidium, cesium, francium, beryllium, magnesium, calcium, strontium, barium, radium, aluminum, gallium, indium, tin, thallium, lead, bismuth, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, or mercury. In some embodiments, a chelator moiety is provided that chelates one or more of magnesium, iron, calcium, manganese, etc. In some embodiments, a magnesium ion chelator is provided.

In some embodiments, chelation moieties and/or components are attached to structural moieties directly (e.g., by covalent linkage). In other embodiments, chelation moieties and/or components are attached to structural moieties indirectly or by a linker. Embodiments are not limited to any particular linker moiety. In some embodiments, the linker connects two moieties (e.g. chelation components and structural moiety). In some embodiments, a linker moiety is cleavable (e.g., chemically cleavable, enzyme cleavable, etc.), such that exposure to appropriate conditions (e.g., cleaving enzyme) cleaves the linker moiety and separates the connected moieties. In some embodiments, the linker moiety is a covalent linkage that is: linear, branched, cyclic, heterocyclic, saturated, unsaturated, or various combinations thereof. In some embodiments, the linker comprises 1-100 non-hydrogen atoms (in addition to hydrogen atoms) selected from the group of C, N, P, O and S (e.g. 1-75, 1-50, 1-40, 1-30, 1-20, 1-10, 1-5, etc.). In some embodiments, the linker comprises any combination of alkyl, ether, thioether, polyether, amine, alkyl, amide, ester, carboxamide, sulfonamide, hydrazide bonds and aromatic or heteroaromatic bonds. In some embodiments, the linker comprises a polymer (e.g. nucleic acid, polypeptide, lipid, or polysaccharide), a peptide linker, a modified peptide linker, a Poly(ethylene glycol) (PEG) linker, a streptavidin-biotin or avidin-biotin linker, polyaminoacids (e.g., polylysine), functionalized PEG, polysaccharides, glycosaminoglycans, dendritic polymers such as described in WO93/06868 and by Tomalia et al. in Angew. Chem. Int. Ed. Engl. 29:138-175 (1990), PEG-chelant polymers such as described in W94/08629, WO94/09056 and WO96/26754, oligonucleotide linker, phospholipid derivatives, alkenyl chains, alkynyl chains, disulfide, or a suitable combination thereof. In some embodiments, a linker moiety comprises any covalent or noncovalent molecular connector capable of stably stringing together a first and second moiety. One of ordinary skill in the art will further appreciate that the above linkers are not intended to be limiting.

C. Structural Moieties

In some embodiments, chelators provided herein comprise structural moieties attached to chelation components that form chelation moieties and sequester metal ions under certain conditions. In some embodiments, structural moieties undergo structural alterations that result in modulation of chelation by regulating formation/deformation of the chelation moiety (from chelation components).

1. Nucleic Acid

In some embodiments, a chelator comprises one or more nucleic acid structural moieties (See, e.g., FIG. 1). In some embodiments, a single chelation component is attached to a nucleic acid strand (See, e.g., FIG. 1A-C). In some embodiments, two or more (e.g., 2, 3, 4, 5, 6, 7, 8, 9, 10, or more) chelation components are attached to a nucleic acid strand (See, e.g., FIG. 1D). In some embodiments, a nucleic acid strand without an attached chelation moiety or component(s) is a structural moiety (e.g., interacting with another structural moiety or structural moieties that are attached to chelation components; See, e.g., FIG. 1D).

Chelation components are attached (e.g., directly or indirectly (e.g., via a linker)) to nucleic acid structural moieties at any suitable position or location that allows for modulation of chelation under varying conditions. In some embodiments, chelation components are attached to the backbone of the nucleic acid strand (e.g., phosphate group, sugar (e.g., ribose, deoxyribose, etc.), etc.). In some embodiments, chelation moieties/components are attached to a base of the nucleic acid strand (e.g., at a modified base). In some embodiments, chelation moieties/components are attached at the terminus of a nucleic acid strand (e.g., 3' OH, 5' phosphate, base, etc.). In some embodiments, chelation moieties/components are attached at an internal position of a nucleic acid strand (e.g., sugar (e.g., ribose, deoxyribose, etc.), base, etc.).

In some embodiments, one or more modified nucleotides incorporated into a nucleic acid structural moiety allow for attachment of chelation components. Exemplary modified nucleotides include those with 5' acrylic phosphoramidite; 5' adenylation; 3'-, 5'-, or internal NHS ester; etc. Other suitable modified nucleotides that are used, in some embodiments, to attach chelation moieties and/or components to structural moieties include, but are not limited to: 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Figure 2A:
Figure 2B:
Figure 2C:
Figure 2D:
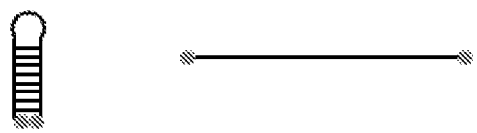
Figure 2E:
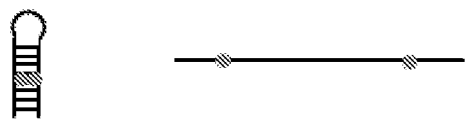
Figure 2F:
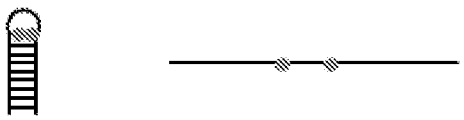

In some embodiments, chelation components are attached to two separate nucleic acid structural moieties (See, e.g., FIG. 2A-C). Under hybridization conditions (e.g., low temperature, high salt concentration, neutral pH), the structural moieties hybridize, bringing the chelation components into close proximity and the appropriate orientation to form a chelation moiety and allow metal-ion chelation. In such embodiments, chelation of metal ions (e.g., efficient chelation of metal ions) is dependent upon the two chelation components being in close proximity and/or adopting a particular orientation. Chelator components in such embodiments are attached at locations on the separate strands that render them unable to chelate metal ions (e.g., incapable of efficient chelation) when the strands are not hybridized, but capable of chelation (e.g., efficient chelation) when the strands are hybridized. In some embodiments, chelation components are located at the 5' and 3' ends of complementary strands, such that they are adjacent when the strands hybridize (See, e.g., FIG. 2A-B). In such embodiments, strands may comprise chelation components at both 3' and 5' ends, such that the duplex has chelation moieties at both ends (See, e.g., FIG. 2B), or each stand comprises a single chelation component to produce a duplex with one chelation moiety (See, e.g., FIG. 2A). In other embodiments, chelation components are within the nucleic acid strands such that the duplex comprises a chelation moiety internal to the strand (See, e.g., FIG. 2C).

In some embodiments, chelation components are attached to two separate locations on a single nucleic acid structural moiety (See, e.g., FIG. 2D-H). Under hybridization and/or folding conditions (e.g., low temperature, high salt concentration, neutral pH), the nucleic acid structural moiety adopts a secondary, tertiary, and/or quaternary structure that brings the chelation components into close proximity and/or into an orientation that allows for formation of a chelation moiety. The present invention is not limited by the types of structures that allow for modulation of chelation. For example, in certain embodiments, under hybridization/folding conditions a nucleic acid structural moiety forms a stem-loop (See, e.g., FIG. 2D-F), pseudoknot (See, e.g., FIG. 2G), triplex, hairpin, bulge loop (e.g., unpaired bases on one side of a helix), interior loop (e.g., unpaired bases on both sides of a helix), two-stem junction (FIG. 2H), etc. Further, the present invention is not limited by the mechanisms through which the secondary, tertiary, or quaternary structure modulates chelation. In some embodiments, chelation components on the 5' and 3' ends of a nucleic acid structural moiety from a chelation moiety when the nucleic acid strand forms a stem-loop (e.g., at low temperature), but separate when the stem-loop is melted (e.g., at high temperature) (See, e.g., FIG. 2D). In other embodiments, chelation components located internally with a nucleic acid strand form a chelation moiety within the stem of a stem-loop, but dissociate when the stem-loop melts (See, e.g., FIG. 2E). In other embodiments, chelation components located internally with a nucleic acid strand form a chelation moiety within the loop of a stem-loop, but dissociate when the stem-loop melts (See, e.g., FIG. 2F). In some embodiments, chelation components located internally with a nucleic acid strand form a chelation moiety upon formation of a pseudoknot, but dissociate when the stem-loop melts (See, e.g., FIG. 2G). In some embodiments, chelation components on the 5' and 3' ends of a nucleic acid structural moiety from a chelation moiety when the nucleic acid strand forms two stem-loops (e.g., at low temperature) thereby placing the chelation components at a two-stem junction, but separate when the stem-loop is melted (e.g., at high temperature) (See, e.g., FIG. 2H).

In some embodiments, a chelator construct comprises a structural moiety without any attached chelation components or chelation moieties, that interacts (e.g., hybridizes) with other structural moieties to modulate chelation (See, e.g., FIG. 2I). For example, in some embodiments, 3' and 5' chelator-components labeled oligonucleotides hybridize to a structural moiety without any attached chelation components to form a two-stem junction that places the chelator components within proximity and in the proper orientation to form a chelator moiety (See, e.g., FIG. 2I). In some embodiments, the chelation moiety on one of the structural moieties (e.g., the 5' chelator-component labeled oligonucleotide) is a phosphate group intrinsic to the oligonucleotide. In some embodiments, the chelation moiety is a 5' phosphate of a nucleic acid.

2. Peptide

In some embodiments, a structural moiety is a peptide or polypeptide. In some embodiments, a structural moiety is a synthetic peptide or polypeptide. In some embodiments, two or more chelation components attached to a single peptide or polypeptide structural moiety are brought together in proper orientation upon folding of the peptide or polypeptide. In other embodiments, chelation components attached to separate peptides and/or polypeptides are brought together to form a chelation moiety upon interaction of the peptides and/or polypeptides.

Chelation components are attached to peptide/polypeptide structural moieties at any suitable position or location that allows for modulation of chelation under varying conditions. In some embodiments, chelation components are attached to an amino acid (e.g., at a modified base). In some embodiments, a synthetic amino acid comprises a chelation component as the R group. In some embodiments, chelation constructs are formed by incorporation of chelation component containing amino acids into peptides and/or polypeptides. In some embodiments, chelation components are attached at the C- and/or N-terminus of a peptide or polypeptide. In some embodiments, chelation moieties/components are attached at an internal position of a peptide or polypeptide strand.

In some embodiments, chelation components are attached to modified or unnatural amino acids incorporated into a peptide or polypeptide. Suitable modified or unnatural amino acids include, but are not limited to: alanine derivatives, alicyclic amino acids, arginine derivatives, aromatic amino acids, asparagine derivatives, aspartic acid derivatives, beta-amino acids, cysteine derivatives, DAB (2,4-diaminobutyric acid), DAP (2,3-diaminopropionic acid), glutamic acid derivatives, glutamine derivatives, glycine derivatives, histidine derivatives, homo-amino acids, isoleucine derivatives, leucine derivatives, linear core amino acids, lysine derivatives, methionine derivatives, n-methyl amino acids, norleucine derivatives norvaline derivatives, ornithine derivatives, penicillamine derivatives, phenylalanine derivatives, phenylglycine derivatives, proline derivatives, pyroglutamine derivatives, serine derivatives, threonine derivatives, tryptophan derivatives, tyrosine derivatives, valine derivatives, etc. (Biochemicals & Reagents for Life Science Research (2004-2005); herein incorporated by reference in their entireties).

In some embodiments, formation of a chelation moiety is modulated by folding/unfolding of the secondary, tertiary, and/or quaternary structure of one or more peptide/polypeptide structural moieties. Any suitable structures and/or interactions of structures may be utilized to modulate chelation within the scope of the invention.

In some embodiments, the formation of protein secondary structure regulates formation of a chelation moiety and modulates chelation. For example, in some embodiments, the formation of an alpha helix, $3_{10}$ helix, or $\pi$ helix brings chelation components together in the proper orientation to form a chelation moiety, but unfolding of the helix separates or misorients the chelation components. In some embodiments, the formation of a beta strand or beta sheet brings chelation components together in the proper orientation to form a chelation moiety, but unfolding of the structure separates or misorients the chelation components. In such embodiments, switching conditions from those that favor secondary structure formation to those that disfavor it (as well as the reverse) allows modulation of chelation efficiency.

In some embodiments, the formation of protein tertiary structure regulates formation of a chelation moiety and modulates chelation. The present invention is not limited by the types of structures that modulate chelation. Suitable structures include alpha sheet, Asx turn, helix-loop-helix, beta bulge, beta hairpin, catgrip, coiled coil, collagen helix, EF hand, Greek key, helix-turn helix, leucine zipper, polyproline helix, ring finger domain, Schellman loop, ST loop, triple helix, zinc finger, or any combinations thereof. In some embodiments, the formation of protein structure brings chelation components together in the proper orientation to form a chelation moiety, but unfolding of the structure separates or misorients the chelation components. In such embodiments, switching conditions from those that favor protein (tertiary) structure formation to those that disfavor it (as well as the reverse) allows modulation of chelation efficiency.

In some embodiments, the formation of protein quaternary structure regulated formation of a chelation moiety and modulates chelation. The present invention is not limited by the types of structures that modulate chelation.

In an exemplary embodiment, a chelation construct comprises two peptides, each with a chelation component attached thereto. Under favorable conditions, each peptide forms an alpha helix, and the helices interact to form a coiled-coil domain. Formation of the coiled-coil brings the chelation components into close proximity and the proper orientation for metal ion chelation. Altering conditions to favor or disfavor formation of the coiled-coil allows modulation of chelation. Similarly, in some embodiments, a leucine zipper interaction brings chelation moieties together under favorable conditions.

In another exemplary embodiment, a chelation construct comprises one peptide with two chelation components attached thereto. Under favorable conditions, the peptide forms an alpha helix, bringing the chelation components into close proximity and the proper orientation for metal ion chelation. However, under conditions in which the alpha helix does not form, the chelation components are misaligned and do not form a chelation moiety. Altering conditions to favor or disfavor formation of the alpha helix allows modulation of chelation.

3. Peptide Nucleic Acid

In some embodiments, a structural moiety is a peptide nucleic acid (PNA). In some embodiments, a single chelation component is attached to a peptide nucleic acid strand. In some embodiments, two or more (e.g., 2, 3, 4, 5, 6, 7, 8, 9, 10, or more) chelation components are attached to a peptide nucleic acid strand. In some embodiments, a peptide nucleic acid strand without an attached chelation moiety or component(s) is a structural moiety (e.g., interacting with another structural moiety or structural moieties that are attached to chelation components).

Chelation components are attached to peptide nucleic acid structural moieties at any suitable position or location that allows for modulation of chelation under varying conditions. In some embodiments, chelation components are attached to the peptide backbone of the peptide nucleic acid. In some embodiments, chelation components are attached to a base of the peptide nucleic acid strand (e.g., at a modified base). In some embodiments, chelation components are attached at the terminus of a peptide nucleic acid strand (e.g., N-terminus or C-terminus). In some embodiments, chelation components are attached at an internal position of a peptide nucleic acid strand.

In some embodiments, one or more modified nucleotides are incorporated into a peptide nucleic acid structural moiety allow for attachment of chelation components. Exemplary modified nucleotides include those with 5' acrylic phosphoramidite; 5' adenylation; 3'-, 5'-, or internal NHS ester; etc. Other suitable modified nucleotides that are used, in some embodiments, to attach chelation components to structural moieties include, but are not limited to: 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

In some embodiments, chelation components are attached to two separate peptide nucleic acid structural moieties). Under hybridization conditions (e.g., low temperature, high salt concentration, neutral pH), the PNA structural moieties hybridize, bringing the chelation components into close proximity and the appropriate orientation to form a chelation moiety and allow metal-ion chelation. In such embodiments, chelation of metal ions (e.g., efficient chelation of metal ions) is dependent upon the two chelation components being in close proximity and/or adopting a particular orientation. Chelator components in such embodiments are attached at locations on the separate PNA strands that render them unable to chelate metal ions (e.g., incapable of efficient chelation) when the strands are not hybridized, but capable of chelation (e.g., efficient chelation) when the strands are hybridized. In some embodiments, chelation components are located at the 5' and 3' ends of complementary strands, such that they are adjacent when the strands hybridize. In such embodiments, PNA strands may comprise chelation components at both 3' and 5' ends, such that the duplex has chelation moieties at both ends, or each stand comprises a single chelation component to produce a duplex with one chelation moiety. In other embodiments, chelation components are within the peptide nucleic acid strands such that the duplex comprises a chelation moiety internal to the strand.

In some embodiments, chelation components are attached to two separate locations on a single peptide nucleic acid structural moiety. Under hybridization and/or folding conditions (e.g., low temperature, high salt concentration, neutral pH), the peptide nucleic acid structural moiety adopts a secondary, tertiary, and/or quaternary structure that brings the chelation components into close proximity and/or into an orientation that allows for formation of a chelation moiety. The present invention is not limited by the types of PNA structures that allow for modulation of chelation.

4. Hybrid Constructs

In some embodiments, a chelator construct comprises structural moieties of two different types of polymers (e.g., PNA and nucleic acid, nucleic acid and peptide, peptide and PNA, etc.). For example, in some embodiments, a PNA structural moiety is attached to a first chelation component, and a complementary nucleic acid structural moiety is attached to a second chelation component; upon hybridization of the PNA and nucleic acid, the chelation moiety is formed. In another exemplary embodiment, a peptide attached to a first chelation component and a nucleic acid, comprising a binding sequence for the peptide, attached to a second chelation component form a chelation moiety upon interaction of the peptide and nucleic acid. The present invention is not limited by the variety of hybrid chelator constructs or the mechanisms for bringing chelation components together to form chelation moieties.

5. Cross-Reactivity

In some embodiments, it is important that structural moieties are not cross-reactive with other components of a reaction that the chelator construct regulates by modulating access to metal ions. For example, nucleic acid sequences are selected for chelator constructs that will not hybridize with primer or target sequences for the amplification reactions the chelator constructs are being employed to regulate. In such embodiments, nucleic acid structural moieties have less than, for example, less than 75% sequence identity (e.g., <70%, <60%, <50%, <40%, <30%, etc.) with nucleic acid sequences (e.g., primer sequences, target sequences, non-target sequences present (or possibly present), etc.) in the reaction mixture. In some embodiments, the same cross-reactivity considerations apply to other types of reactions and other types of structural moieties (e.g., peptide, PNA, etc.). For example, peptide structural moieties are selected that do not interact with, for example, protein or nucleic acid components of a reaction mixture.

In some embodiments, structural moieties are not cross-reactive with human DNA and/or other DNA sequences being amplified in a reaction being modulated by a chelator construct.

D. Exemplary Embodiments

Figure 3:
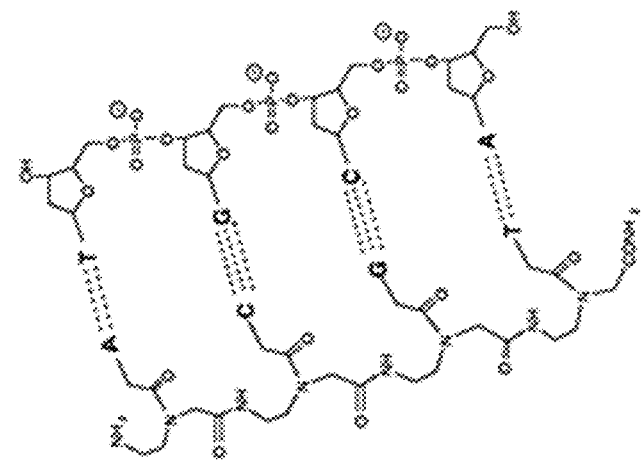
FIG. 3 shows exemplary structural moieties.
Figure 3:
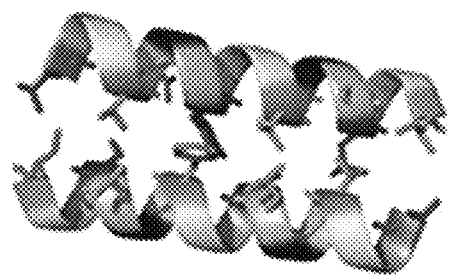
Figure 3:
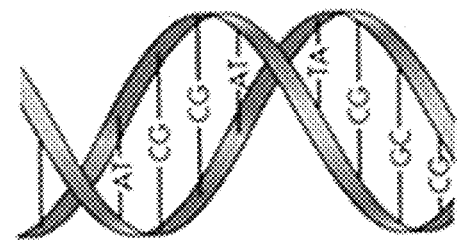

In certain embodiments, a chelator construct is a zipper chelator. As used herein, a zipper chelator comprises two strands (e.g., separate strands or distally linked by a loop or other connection) that interact under favorable conditions through noncovalent interactions (e.g., hydrogen bonding, hydrophobic interactions, etc.) along their length to stably align the two stands (See, e.g., FIG. 3). The strands of a zipper chelator may be protein, nucleic acid, peptide nucleic acid, and/or other suitable polymers or molecular components. Suitable chelation components and structural moieties for a zipper chelator are described in sections C1-C4 above.

Under conditions that disfavor or destabilize interactions between the strands, the chelation components are separated. Conditions that favor interactions between the strands include low(er) temperature (e.g., below the $T_m$ of the strands). In some embodiments, at sufficiently low temperature, the chelation moiety is maximally formed, resulting in the minimal $K_d$ for the appropriate metal ions. As temperature is raised, the interaction between the strands is destabilized, and the $K_d$ of the chelation moiety for metal ions rises. In such embodiments, the $K_d$ of the chelation moiety is modulated by raising and lowering the temperature of the system. For example, given the appropriate ratio of chelation moieties to metal ions (e.g., excess chelation moieties), at low temperature all the available metal ions (e.g., $Mg^{2+}$) are sequestered; however, as the temperature of the system is raised, the $K_d$ of the chelation moiety rises, and at a certain temperature free metal ions (e.g., Mg2+) are available in solution. By adjusting the temperature of the system, the concentration of free metal ions (e.g., $Mg^{2+}$) in solution is modulated.

Figure 5:
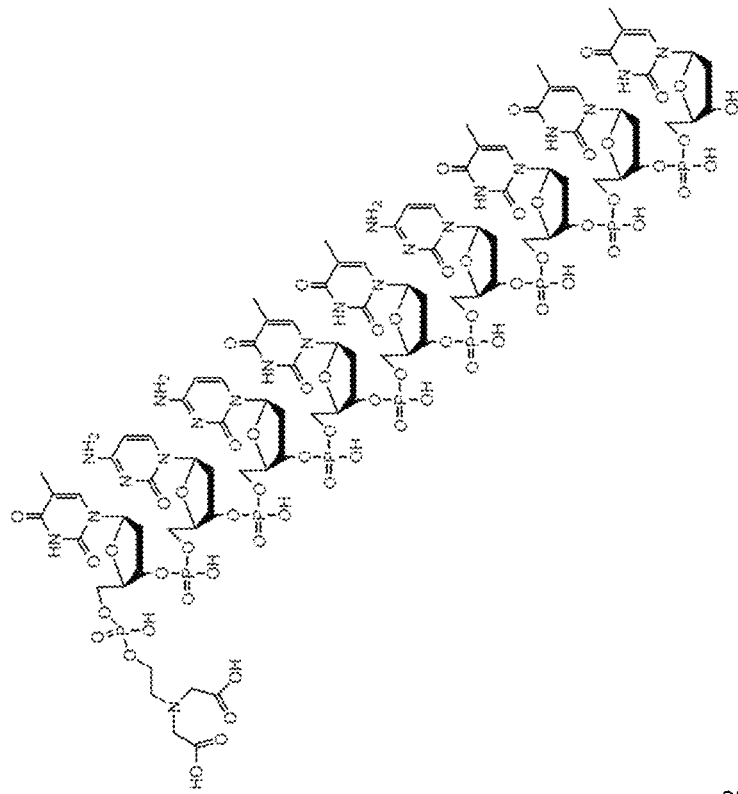
FIG. 5 shows an exemplary chelator construct comprising three nucleic acid structural moieties.
Figure 5:
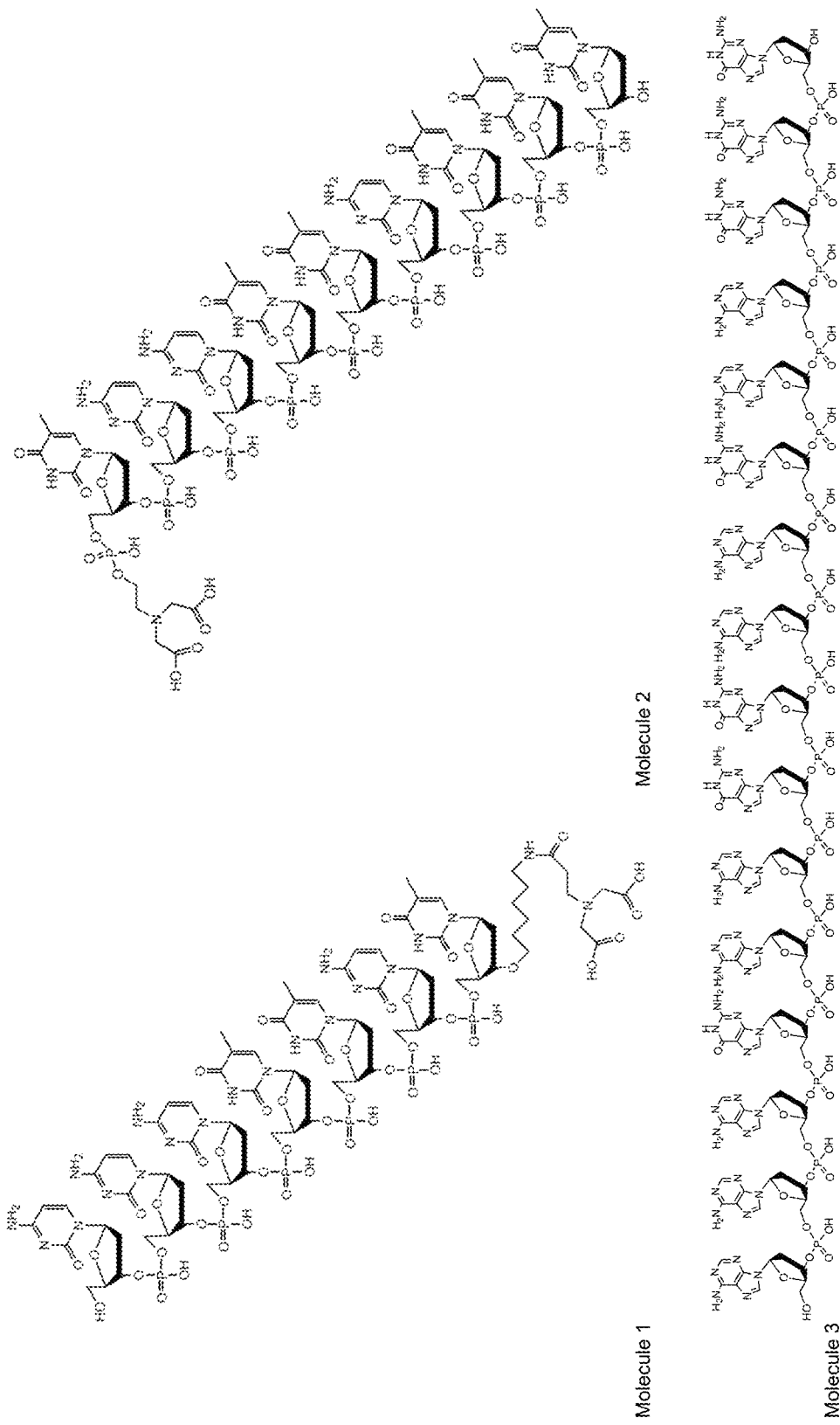
Figure 6:
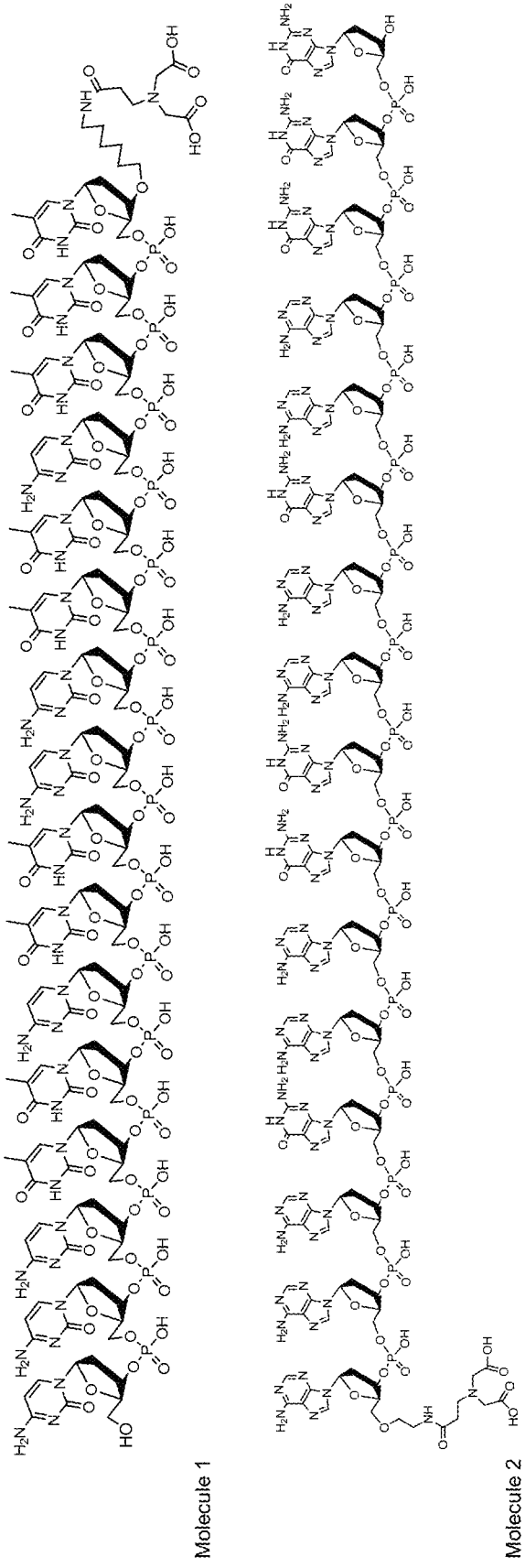
FIG. 6 shows an exemplary chelator construct comprising two nucleic acid structural moieties.

Exemplary chelator constructs comprising three and two structural moieties are provided in FIG. 5 and FIG. 6, respectively.

E. Conditions/Modulation

Chelation constructs are provided herein that efficiently chelate metal ions under one set of conditions, but are poor chelators under a second set of conditions. In some embodiments, altering the conditions alters the dissociation constant ($K_d$) for the metal ion.

In some embodiments, under metal ion sequestering conditions, a chelation construct has a $K_d$ for a target metal ion between 1 fM and 100 µM (e.g., 1 fM . . . 10 fM . . . 100 fM . . . 1 µM . . . 10 µM . . . 100 µM . . . 1 mM . . . 10 nM . . . 100 nM . . . 1 µM . . . 10 µM . . . 100 µM). In some embodiments, under non-sequestering conditions, a chelation construct has a $K_d$ for a target metal ion above, for example 1 µM (e.g., >1 µM . . . >10 µM . . . >100 µM . . . >1 mM . . . >10 mM . . . >100 mM, or more). In some embodiments, depending upon the desired application and the metal ion concentration to be used, a chelator construct with an appropriate sequestering and non-sequestering $K_d$ is designed, selected, provided, etc.

A variety of conditions may alter the favorability structure formation, hybridization, etc. of structural element(s), and therefore modulate formation of the chelator moiety. These conditions include, but are not limited to, temperature, salt concentration, solvent, pH, presence/absence/concentration of denaturants, etc.

In some embodiments, elevation of temperature disfavors the formation of secondary, tertiary and quaternary structures in proteins, nucleic acids, peptide nucleic acids, and hybrids thereof. Therefore, in some embodiments, a chelator construct sequesters metal ions at lower temperatures, but does not at higher temperatures. In some embodiments, the transition from sequesterer to non-sequesterer occurs at the melting temperature ($T_m$) of the modulating structure (e.g., 30° C. . . . 35° C. . . . 40° C. . . . 45° C. . . . 50° C. . . . 55° C. . . . 60° C. . . . 65° C. . . . 70° C. . . . 75° C. . . . 80° C. . . . 85° C. . . . 90° C., or more). In some embodiments, depending upon the structure involved and the type of structural moiety, the transition may be gradual (e.g., creating a $K_d$ gradient) or rapid (e.g., creating a steep transition from sequestering to non-sequestering).

In some embodiments, other factors and conditions, including pH, salt concentration, the presence/absence of denaturants, solvent type, etc. are used to alter the $T_n$, of structural moieties or to create an alternate set of conditions to modulate chelation (e.g., neutral vs. high pH, low vs. high salt concentration, etc.).

F. Applications

The present invention finds use in any application where metal ions in solution are desirable under one set of conditions, but undesirable under a second set of conditions. In some embodiments, the chelator constructs described herein allow modulation of metal ion concentration over the course of time (e.g., by altering the conditions).

Specific metal ions are required for the activity of many enzymes and are therefore required reagents in many assays, reactions, etc. For example, magnesium is required as a co-factor for thermostable DNA polymerase (and many other enzymes). Taq DNA polymerase is a magnesium-dependent enzyme and an optimum magnesium concentration is required for the success of polymerase chain reaction (PCR). However, magnesium is also a co-factor for the exonuclease activity of Taq DNA polymerase. Therefore, the presence of magnesium can result in degradation of the reactants (e.g., nuclease degradation of primers, substrates, and/or products) or products of a PCR reaction. Similarly, magnesium is required for the activity of RNA polymerase, but it has been demonstrated that RNA is non-specifically degraded in the presence of magnesium ions. Therefore, in both of these exemplary cases, a reversible magnesium ion chelator allows for magnesium ions to be present in solution at temperatures where DNA or RNA polymerization occur (or other enzymatic reactions), but once the temperature is reduced following the polymerization reaction, the magnesium is sequestered to prevent product degradation.

In exemplary embodiments, a nucleic acid (e.g., DNA, RNA, etc.) chelator sequesters $Mg^{+2}$ from DNA polymerase (e.g., Taq DNA polymerase or proofreading Pfu DNA polymerase) or RNA polymerase at any temperature below the melting temperature of the secondary or tertiary structure of the nucleic acid, preventing polymerization from occurring or the reactants (e.g., nuclease degradation of primers, substrates) and/or products from being degraded (See FIG. 7A). Upon increase in temperature above the melting point, the structure of the chelator construct is altered, raising the $K_d$ of the chelator for $Mg^{2+}$. Free $Mg^{2+}$ is thereby released into solution allowing the reaction (e.g., PCR) to start (FIG. 7B). When the temperature is lowered again, the chelator structure reforms and $Mg^{2+}$ is again unavailable (e.g., for PCR). The sequestration of $Mg^{2+}$ prevents exonuclease activity and non-specific degradation of the products. In the absence of modulatable chelators and at low temperature, secondary polymerization products form and the polymerase exonuclease is active degrading primers and template (FIG. 7C). When the temperature is raised, in the absence of a modulatable chelator, the amplification quality is affected by accumulation of secondary products, primer dimers and decreased yield (FIG. 7D). When the temperature is lowered again, the polymerase and exonuclease domains remain active leading to additional degradation of PCR products and reactants.

Similar condition-specific sequestration of metal ions finds use in regulating the activity of other enzymes. Chemical reactions dependent upon the presence of metal ions in solution are also regulated using chelator constructs described herein.

Figure 4:
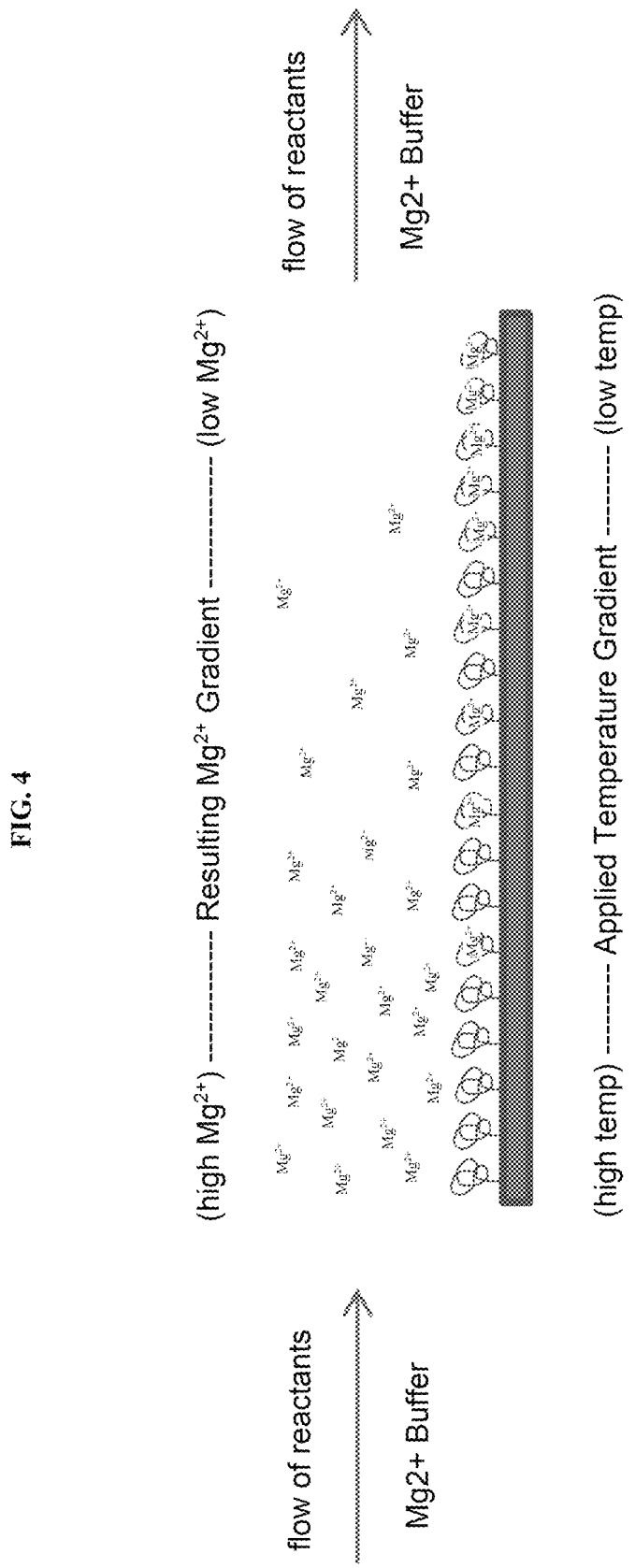
FIG. 4 shows an exemplary application of the chelator constructs described herein; a plurality of chelators are used to create a metal ion gradient across a surface.

In other embodiments, a plurality of reversible chelation constructs is used to provide a metal-ion gradient across a volume or a surface. For example, reversible chelation constructs described herein are attached to a surface (e.g., solid support, microchannel, well, tube, etc.) or embedded within a gel or other environment (See, e.g., FIG. 4). Different portions of the surface, gel, or other environment are exposed to different conditions (e.g., structure promoting, structure disfavoring, etc.), thereby creating regions of the surface, gel, or other environment that are metal-ion chelating regions and other regions that have metal ions free in solution. Applying a gradient of conditions (e.g., temperature gradient) across the surface, gel, or other environment results in a metal-ion gradient (See, e.g., FIG. 4). In some embodiments, as enzymes and/or reactants are passed over or through the metal-ion gradient, reactions are proceed or are halted, depending upon the region conditions (e.g., structure promoting, structure disfavoring, etc.) of the environment. Such metal ion gradients may find use, for example, in NextGen sequencing applications, or other applications in which a single buffer supports multiple reaction steps (e.g., lysis, purification, ligation of adapters or other components, etc.). Other embodiments in which chelator constructs are immobilized to a surface are also contemplated.

In some embodiments, chelator constructs are used to create hot-start conditions for an enzyme. For example, a chelator construct that chelates metal ion X up to temperature Y, and an enzyme that is dependent upon metal ion X for its activity are provided in a reaction mix with the other necessary reactants. The enzyme will not catalyze the reaction until the chelator releases the metal ion X. Therefore, the reaction will only take place when the temperature of the reaction mix is brought above temperature Y. Such a setup allows for a user to apply an artificial hot-start (temperature Y) to an enzyme that would otherwise work at lower temperatures.

In some embodiments, chelator constructs are used to modulate the activity of proteases or other enzymes. For example, a chelator construct with temperature-modulatable affinity for zinc ions is used to modulate the activity of Zn-dependent proteases. The chelator construct chelates Zn ions up to temperature X; therefore, the protease that is dependent upon Zn for activity will not catalyze proteolysis at temperature X or below. Above temperature X, the structural moiety of the chelator construct denatures or unfolds, misorienting the chelation components and releasing Zn ions into solution. Under such conditions, the protease has access to ample Zn ions and proteolysis occurs. Such a mechanism of enzyme-activity modulation is not limited to proteases and/or enzymes dependent upon Zn. Modulation of other enzyme activities via selective chelation of any suitable metal ions is contemplated.

In some embodiments, chelator constructs are used to modulate copper catalyzed click chemistry reactions (*Development and Applications of Click Chemistry* Gregory C. Patton Nov. 8, 2004; herein incorporated by reference in its entirety). The reaction requires a copper catalyst and therefore only occurs under the low affinity conditions when the copper is not bound by the chelator. When the efficient chelator is present (i.e. at low temperature), there is insufficient copper concentration to catalyze the click reaction.

In some embodiments, chelator constructs are used to modulate calcium dependent signaling. Many cellular processes are responsive to extracellular calcium concentration, and a reversible chelator can be used to release calcium under one set of conditions and to sequester the calcium under a second set of conditions. This could be used to provoke or inhibit a cellular response of interest.

EXPERIMENTAL

Example 1: Chelator Compatibility with PCR

To demonstrate compatibility chelators of the present invention with PCR, a 360 bp fragment of the human α-1 antitrypsin gene is amplified.

The amplifications are assembled on ice or a cold block. The magnesium chelators are titrated (0.75, 1.5, 3.0 and 4.5 mM) into reactions with the following composition: 1× GoTaq® Colorless Flexi Buffer (Promega Corporation), 1.5 mM $MgCl_2$, 200 µM each dNTP, 1 µM Forward and Reverse primer, 0.025 U/µl GoTaq® DNA Polymerase (Promega Corporation), 3.3 ng human genomic DNA and nuclease-free water to bring it to a 50 µl reaction. No chelator control, no template control, and no primer control (to ensure that a DNA portion of the chelator, if present, does not serve as a primer) reactions are also assembled. The reactions are put into a thermal cycler once the ramping for the initial denaturing cycle reaches >80° C. The following cycling protocol is used: 1 cycle (95° c. for 2 minutes), 35 cycles (95° C. for 15 seconds, 65° C. for 30 seconds), 1 cycle (72° C. for 5 minutes) and 4° soak. Once cycling is complete, PCR products are separated and visualized on a 2% agarose gel stained with ethidium bromide and UV-light illumination. A camera is used to record the image of the gel. Template titrations (33, 3.3, 0.33, 0.033 ng DNA/50 µl reaction) are done to access the amount of inhibition by the chelators by looking at sensitivity.

Expected Results:
1. In the no chelator control, a 360 bp product is observed.
2. In reactions with a chelator that does not inhibit or is compatible with PCR, a 360 bp product is observed.
3. In reactions with a chelator that is not compatible or inhibits amplification, little or no amplification product should be observed. Increasing chelator results in decreased PCR yield.
4. With the no template and no primer controls, no amplification is observed.

Example 2: Chelators Provide Hot-Start for Amplification

To demonstrate that the chelators of the present invention can provide hot-start amplification, a 1.5 kb fragment of the Corynephage omega gene from plasmid DNA is amplified. If there are hot-start conditions, e.g., the magnesium is chelated at lower temperatures which inhibit DNA polymerase (e.g., Taq polymerase) which then is released at temperatures needed for amplification; the amplification will produce a single product that is approximately 1.5 kb in size. If there are not hot-start conditions, e.g., the magnesium is not chelated at lower temperatures, and the DNA polymerase is not inhibited, the amplification will produce a product that is approximately 400 bp, with possibly other secondary products, and the 1.5 kb fragment may or may not be present. To rigorously test the ability of the chelator(s) to bind magnesium and thus inhibit DNA polymerase (e.g., Taq DNA polymerase) activity, the amplification reactions are incubated at 22° C. for six hours prior to performing PCR amplification.

The amplifications are set up at room temperature. The magnesium chelator(s) are titrated (1.25, 2.5, 5.0 and 7.5 mM) into reactions with the following composition: 1× GoTaq® Colorless Flexi Buffer, 2.5 mM $MgCl_2$, 200 µM each dNTP, 0.4 µM each primer, 0.025 U/µl GoTaq® DNA Polymerase, 500 µg plasmid DNA and nuclease-free water to bring it to a 25 µl reaction. A "no chelator", "no template", "no primer" (to ensure that the DNA portion, if present in the chelator being tested, does not serve as a primer) and "positive hot-start" (using GoTaq® DNA polymerase with an antibody mediated hot-start) control reactions are assembled. The reactions are put in a room temperature thermal cycler, and the following cycling protocol is used: 1 cycle (22° C. for 6 hours, 95° C. for 2 minutes), 30 cycles (93° C. for 15 seconds, 54° C. for 30 seconds, 72° C. for 1 minute), 1 cycle (72° C. for 5 minutes), and 4° C. soak. Once cycling is complete, PCR products are separated and visualized on a 1% agarose gel with ethidium bromide staining and UV-light illumination. A camera is used to record the image of the gel.

Expected Results:
1. In hot-start control (using antibody mediated hot-start DNA polymerase) and with chelator(s) exhibiting hot-start-ability, reactions produce a single 1.5 kb product.
2. In chelator control and with chelator(s) not exhibiting hot-start ability, reactions produce a 400 bp product. Other secondary products and the 1.5 kb product may or may not be present.
3. In the "no template" and "no primer" controls, no amplification occurs.

Example 3: Thermal Reversibility

A. Evaluation of Reversibility from Low to High Temperature and Back to Low Temperature with Stopped Reactions Activity assay reactions are assembled with and without chelator. Reactions are incubated at low temperature (e.g., 22° C. or 37° C.) for a period of time. Aliquots are removed, reactions stopped and samples processed. Temperatures of remainder of reactions are increased to 68-79° C., and incubated for a given amount of time. Aliquots are removed, reactions stopped and samples processed. The temperature of remainder of the reactions is lowered to the low temperature (e.g., 22° C. or 37° C.) and incubated for an amount of time. Aliquots are removed, reactions stopped and samples processed.

This method finds use with endpoint activity assay methods. Examples of activity assays that could be used are as follows.

1. A DNA polymerase activity assay monitoring radioactive incorporation where "activated" calf thymus or salmon sperm DNA is used as the DNA substrate. Along with DNA substrate, the reactions minimally contain a buffer (e.g., GoTaq® buffer), magnesium, dNTPs and polymerase. Reactions are stopped with EDTA, DNA precipitated by ice-cold TCA (tricholoracetic acid), incubated on ice for at least 10 minutes, filtered using GF/C filters and radioactive incorporation in precipitable DNA on filter is measured by scintillation counting. (Apospian & Kornberg. (1962) JBC 237: 519-525; Chien et al. (1976) J. Bact. 127: 1550-1557; herein incorporated by reference in their entireties).
2. A primer extension DNA polymerase activity assay monitoring radioactive incorporation where single-stranded DNA (e.g., M13) and primer substrate is used as the DNA substrate. The primer and template are annealed, and reactions minimally contain buffer (e.g., GoTaq® buffer), magnesium, dNTPs and polymerase. Reactions are stopped with EDTA, DNA precipitated by ice-cold TCA, incubated on ice for at least 10 minutes, filtered using GF/C filters and radioactive incorporation in precipitable DNA on filter is measured by scintillation counting. (Longley & Mosbaugh. (1991) Biochemistry 30: 2655-2664; herein incorporated by reference in its entirety).
3. A 5' nuclease assay (for an enzyme such as Taq) where a 5' fluorescently dye-labeled bifurcated duplex DNA substrate is used (Lyamichev et al. (1993) Science 260: 778-783; Lyamichev (1999) PNAS 96:6143-6148; Ceska & Sayers (1998) TIBS: 331-336; herein incorporated by reference in their entireties). The DNA substrate is annealed and combined with reaction components including buffer (e.g., GoTaq® buffer), magnesium and nuclease or polymerase with nuclease domain. Reactions are stopped with EDTA and run on a capillary electrophoresis instrument to determine amount of cut and uncut DNA substrate.
4. A 3' to 5' exonuclease (for a proofreading polymerase such as Pfu) assay where 3'-radiolabeled duplexed DNA is used as a substrate. The DNA substrate is combined with reaction components including buffer (e.g., GoTaq® buffer), magnesium and nuclease or polymerase with nuclease domain. Reactions are stopped by EDTA, DNA precipitated by ice-cold TCA and incubated on ice for at least 10 minutes. Precipitable DNA is pelleted by centrifugation and released non-precipitable DNA from radioactively labeled 3' end is measured by scintillation counting (Chase & Richardson. (1974) JBC 249: 4545-4552; Sambrook et al. (1989) Molecular Cloning: A Laboratory Manual (2nd Edition). Pages 10.51-52; herein incorporated by reference in their entireties).

Expected Results:
1. During the first low temperature incubation, the chelator and cation are bound. For reactions with chelator, little or no activity/product accumulation is expected. For reactions without chelator, activity/product accumulation characteristic of low temperature incubation is expected.
2. During the high temperature incubation, the cation and chelator are not bound. For reactions with and without chelator, a high amount of activity/product accumulation is expected. The amount of activity/product accumulation should be similar for reactions with and without chelator.
3. During the second low temperature incubation, the chelator and cation are bound again. For reactions with chelator, little or no activity/product accumulation is expected. For reactions without chelator, activity/product accumulation characteristic of low temperature incubation is expected.

B: Evaluation of Reversibility from Low to High Temperatures and Back to Low Temperature with a Real-Time Extension Rate Assays This method is similar to A except it uses a real-time extension rate activity assay method to measure nucleotide incorporation of a DNA polymerase. An example of this would be a primer extension assay where extension is monitored on a real-time PCR instrument using noncovalent DNA dyes such as BRYT™ Green or SYBR® Green and oligonucleotide DNA substrate (Montgomery & Wittwer. (2014) Clinical Chemistry 60(2):334-340); herein incorporated by reference in its entirety). Activity assay reactions are assembled with and without chelator. The reactions minimally include buffer (e.g., GoTaq® buffer), magnesium, dNTPs, DNA substrate and polymerase. The reactions are incubated at low temperature (e.g., 22° C. or 37° C.) for a given period of time measuring extension rate. Temperatures of reactions are then increased to 68-79° C. and incubated for a given amount of time measuring extension rate. Temperature of the reactions are then lowered to the low temperature (e.g., 22° C. or 37° C.) and incubated for a given amount of time measuring extension rate.

Expected Results:
1. During the first low temperature incubation, the chelator and cation are bound. For reactions with chelator, low or no activity/extension rate is expected. For reactions without chelator, activity/extension rate characteristic of low temperature incubation is expected.
2. During the high temperature incubation, the cation and chelator are not bound. For reactions with and without chelator, high activity/extension rate is expected. The extension rate is similar for reactions with and without chelator.
3. During the second low temperature incubation, the chelator and cation are bound again. For reactions with chelator, low or no activity/extension rate is expected. For reactions without chelator, activity/extension rate characteristic of low temperature incubation is expected.

C: Evaluation of Reversibility, Ruggedness and Stability of Chelator in PCR

The 5' nuclease activity of Taq DNA polymerase at low temperature is used to monitor chelator and cation binding before and after amplification reactions. The amplification monitors the availability of magnesium at higher temperatures. Amplification reactions are assembled with and without chelators. Reactions include minimally buffer (e.g., GoTaq® buffer), magnesium, dNTPs, primers, plasmid template and polymerase. Hot-start PCR amplification of Corynephage omega gene could be used.

For set 1 of the reactions, 5' fluorescently dye-labeled bifurcated duplex DNA substrate (see A, assay example 3) is added to reactions. Reaction is incubated at room temperature or 4° C. for a period of time. Reactions are stopped with EDTA and analyzed by capillary electrophoresis to determine the amount of cut and uncut DNA substrate.

For set 2 of the reactions, reactions are incubated at room temperature or 4° C. for period of time in parallel with set 1. Reactions are then incubated in a thermal cycler using the following cycling program [1 cycle (22° C. for 6 hours, 95° C. for 2 minutes), 30 cycles (93° C. for 15 seconds, 54° C. for 30 seconds, 72° C. for 1 minute), 1 cycle (72° C. for 5 minutes), and 4° C. soak]. Separate and visualize PCR products on a 1% agarose gel stained with ethidium bromide and UV-light. A camera is used to record the gel image.

For set 3, reactions are incubated at room temperature or 4° C. for period of time then amplified as done with set 2 (reactions done in parallel). Next, 5' fluorescently dye-labeled bifurcated duplex DNA substrate is added and reactions are incubated at room temperature or 4° C. for period of time. Reactions are stopped with EDTA and analyzed by capillary electrophoresis to determine the amount of cut and uncut DNA substrate.

Expected Results:
1. With chelator (if reversible)
    For the first set of reactions incubated at low temperature, no cutting of 5' labeled DNA substrate is expected. The 5' nuclease activity of Taq DNA polymerase is inhibited.
    For the second set of reactions incubated at low temperature then amplified, only a 1.5 kb product in hot-start amplification is expected. The 400 bp or secondary PCR products is not observed, since magnesium is not available at low temperature, but is available at high temperature making amplification possible.
    For the third set of reactions subjected to low temperature, amplification and then the second low temperature incubation, no cutting of 5' labeled DNA substrate is expected. The 5' nuclease activity of Taq DNA polymerase is inhibited again. If the chelator does not survive PCR intact, then the 5' labeled DNA substrate will be cut.
2. With chelator (if not reversible)
    For the first set of reactions incubated at low temperature, no cutting of 5' labeled DNA substrate is expected. The 5' nuclease activity of Taq DNA polymerase is inhibited.
    For the second set of reactions incubated at low temperature then amplified, no amplification is expected.
    For the third set of reactions subjected to low temperature, amplification and then the second low temperature incubation, no cutting of the 5' labeled DNA substrate is expected.
3. Without chelator
    For the first set of reactions incubated at low temperature, the 5' labeled DNA substrate is expected to be cut at levels appropriate for that temperature. The 5' nuclease activity of Taq DNA polymerase is not inhibited.
    For the second set of reactions incubated at low temperature then amplified, the 400 bp product, indicating no hot-start amplification since magnesium is available at low and high temperature, is expected. Other secondary products may be observed.
    For the third set of reactions subjected low temperature incubation, amplification and then the second low temperature incubation, the 5' labeled DNA substrate is expected to be cut. The 5' nuclease activity of Taq DNA polymerase is not inhibited D: Hot-Start Model PCR Reversibility The amplification experiment above to demonstrate that the chelator(s) allow hot-start amplification also demonstrates reversible binding of the chelator and cation. At low temperature, if the chelator and magnesium are bound, the polymerase cannot generate spurious products since there is no available magnesium. Only a single 1.5 kb PCR product is made. At high temperature, if the magnesium is free, then amplification products will be generated. If the magnesium and chelator were not dissociated, then products would not be formed since reaction requires magnesium.

E: Reversibility and Easy Visualization of Temperatures where Chelator and Magnesium are or are not Bound.

Restriction enzyme digests are assembled with DNA substrate containing a restriction enzyme cut-site and using enzymes that have activity over a broad temperature range, e.g., BstXI and BssHII. BstXI and BssHII have temperature optima at 50° C., but retain 75-100% of their activity at 37° C. and are not or are only slightly heat inactivated at 65° C. These enzymes also require magnesium. Reactions include the specific restriction endonuclease buffer, magnesium, DNA substrate and enzyme. Reactions are stopped by the addition of EDTA.

The restriction enzyme digests are tested and compared with and without chelator at different temperatures and incubation times. The restriction digest products are separated and visualized on an agarose gel stained with ethidium bromide and UV-light illumination. A camera is used to record image of gel. Accumulation or lack of accumulation of cleavage product is observed.

Expected Results:
1. If the chelator binds magnesium at lower temperatures, there is no cutting of the DNA substrate. Without a chelator, there is cleavage of the DNA substrate.
2. As the temperature is increased and the chelator and magnesium start to dissociate, there is cleavage in the reactions containing chelator, and there cleavage continues in reactions without chelator.
3. When the temperature is high enough, the chelator and magnesium are completely dissociated, and reactions with and without chelator exhibit similar levels of cleavage.
4. To show reversibility from high to low temperature, the reactions can be switched to a low temperature. Reactions with chelator will stop accumulating cleaved substrate, but reactions without chelator will continue to accumulate product.

All publications and patents mentioned in the present application are herein incorporated by reference in their entireties. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A reversible chelator construct comprising:
   (a) a first nucleic acid strand attached to a first chelation component at the 5' terminus of the first nucleic acid strand;
   (b) a second nucleic acid strand attached to a second chelation component at the 3' terminus of the second nucleic acid strand; and
   (c) a third nucleic acid strand;
   wherein, when under low temperature conditions, the construct adopts a first conformation in which the first and second nucleic acid strands hybridize to the third nucleic acid strand;
   wherein, when under high temperature conditions, the construct adopts a second conformation in which the first and second nucleic acid strands are not hybridized to the third nucleic acid strand;
   wherein, when the first and second nucleic acid strands are hybridized to the third nucleic acid strand, the first and second chelation components are placed into appropriate proximity and orientation to more efficiently chelate metal ions than when the first and second nucleic acid strands are not hybridized to the third nucleic acid strand; and wherein, wherein the first and second nucleic acid strands are not hybridized to the third nucleic acid strand, the first and second chelation components chelate metal ions less efficiently than when the first and second nucleic acid strands are hybridized to the third nucleic acid strand.

2. The reversible chelator construct of claim 1, wherein the first and second chelation components are iminodiacetic acid moieties.

3. The reversible chelator construct of claim 1, wherein the high temperature is a temperature above a transition temperature between the first and second confirmations and the low temperature is a temperature below a transition temperature between the first and second confirmations.

4. The reversible chelator construct of claim 1, wherein the chelation components have a $K_d$ of 100 μM or more for a metal ion when in the second conformation.

5. The reversible chelator construct of claim 1, wherein the chelation components have a $K_d$ of 100 nM or less for a metal ion when in the first conformation.

6. A method of regulating an enzymatic reaction comprising:
 (a) providing in a reaction mix:
  (i) an enzyme that catalyzes said enzymatic reaction, wherein said enzyme requires a metal ion cofactor for catalysis;
  (ii) a substrate for said enzyme;
  (iii) the metal ion cofactor for said enzyme; and
  (iv) a reversible chelator construct of claim 1;
 (b) exposing said reaction mix to a first set of conditions comprising the low temperature of claim 1, wherein said enzyme inefficiently catalyzes said enzymatic reaction under said first set of conditions because said metal ion cofactor is chelated by the reversible chelator construct; and
 (c) exposing said reaction mix to a second set of conditions comprising the high temperature of claim 1, wherein said enzyme efficiently catalyzes said enzymatic reaction under said second set of conditions because said metal ion cofactor is available in solution.

7. The method of claim 6, wherein step (b) is performed before step (c).

8. The method of claim 7, wherein further comprising:
 (d) repeating step (b).

9. The method of claim 6, wherein step (c) is performed before step (b).

10. The method of claim 9, wherein further comprising:
 (d) repeating step (c).

11. The method of claim 6, wherein said enzyme is DNA polymerase, said metal ion cofactor is magnesium, and said enzymatic reaction is polymerase chain reaction, 3' to 5' cleavage of nucleic acids, or 5' to 3' cleavage of nucleic acids.

12. The method of claim 6, wherein inefficient catalysis is less than 10% enzyme activity.

13. The method of claim 6, wherein efficient catalysis is greater than 75% enzyme activity.

* * * * *

SEQUENCE LISTING

```
<160> NUMBER OF SEQ ID NOS: 5

<210> SEQ ID NO 1
<211> LENGTH: 7
<212> TYPE: DNA
<213> ORGANISM: Artificial sequence
<220> FEATURE:
<223> OTHER INFORMATION: Synthetic

<400> SEQUENCE: 1 cccttct                                                                   7

<210> SEQ ID NO 2
<211> LENGTH: 9
<212> TYPE: DNA
<213> ORGANISM: Artificial sequence
<220> FEATURE:
<223> OTHER INFORMATION: Synthetic

<400> SEQUENCE: 2 tccttcttt                                                                 9

<210> SEQ ID NO 3
<211> LENGTH: 16
<212> TYPE: DNA
<213> ORGANISM: Artificial sequence
<220> FEATURE:
<223> OTHER INFORMATION: Synthetic

<400> SEQUENCE: 3
aaagaaggaa gaaggg                                                        16

<210> SEQ ID NO 4
<211> LENGTH: 16
<212> TYPE: DNA
<213> ORGANISM: Artificial sequence
<220> FEATURE:
<223> OTHER INFORMATION: Synthetic

<400> SEQUENCE: 4
cccttcttcc ttcttt                                                        16

<210> SEQ ID NO 5
<211> LENGTH: 16
<212> TYPE: DNA
<213> ORGANISM: Artificial sequence
<220> FEATURE:
<223> OTHER INFORMATION: Synthetic

<400> SEQUENCE: 5
aaagaaggaa gaaggg                                                        16
```